(12) United States Patent
Tjøtta et al.

(10) Patent No.: US 6,852,749 B1
(45) Date of Patent: Feb. 8, 2005

(54) PYRAZOLIDINOL COMPOUNDS

(76) Inventors: Enok Tjøtta, c/o A-Viral AS, Karihaugveien 102, N-1006 Oslo (NO); Jo Klaveness, c/o A-Viral AS, Karihaugveien 102, N-1006 Oslo (NO)

( * ) Notice: Subject to any disclaimer, the term of this patent is extended or adjusted under 35 U.S.C. 154(b) by 246 days.

(21) Appl. No.: 10/019,229

(22) PCT Filed: Jun. 29, 2000

(86) PCT No.: PCT/GB00/02513

§ 371 (c)(1),
(2), (4) Date: May 29, 2002

(87) PCT Pub. No.: WO01/00585

PCT Pub. Date: Jan. 4, 2001

(30) Foreign Application Priority Data

Jun. 29, 1999 (GB) ............................................. 9915184

(51) Int. Cl.$^7$ ..................... A61K 31/4152; A61P 29/00
(52) U.S. Cl. ..................................... 514/404; 548/366.4
(58) Field of Search .......................................... 514/403

(56) References Cited

U.S. PATENT DOCUMENTS 4,169,147 A * 9/1979 Bodor et al. ................ 514/403

\* cited by examiner

*Primary Examiner*—Robert W. Ramsuer
(74) *Attorney, Agent, or Firm*—Dechart LLP; John W. Ryan

(57) ABSTRACT

The invention provides the use of an optionally hydroxy-protected 4-hydroxyo or hydroperoxy-3,5-dioxopyrazolidine or an equivalent wherein a pyrazolidine ring attached oxygen is replaced by a sulphur, or a physiologically acceptable salt thereof, for the manufacture of a medicament for use in therapy or prophylaxis. Additionally, the invention provides a method of combating HIV infection which comprises administering to an HIV-infected patient a T-lymphocyte growth suppressing agent, preferably a pyrazolidinol, in an amount sufficient to suppress T-lymphocyte growth in said patient for a period sufficient to reduce the T-lymphocyte concentration in lymph nodes in said patient by at least 25%, said administration being repeated at intervals of at least 3 months.

5 Claims, 5 Drawing Sheets

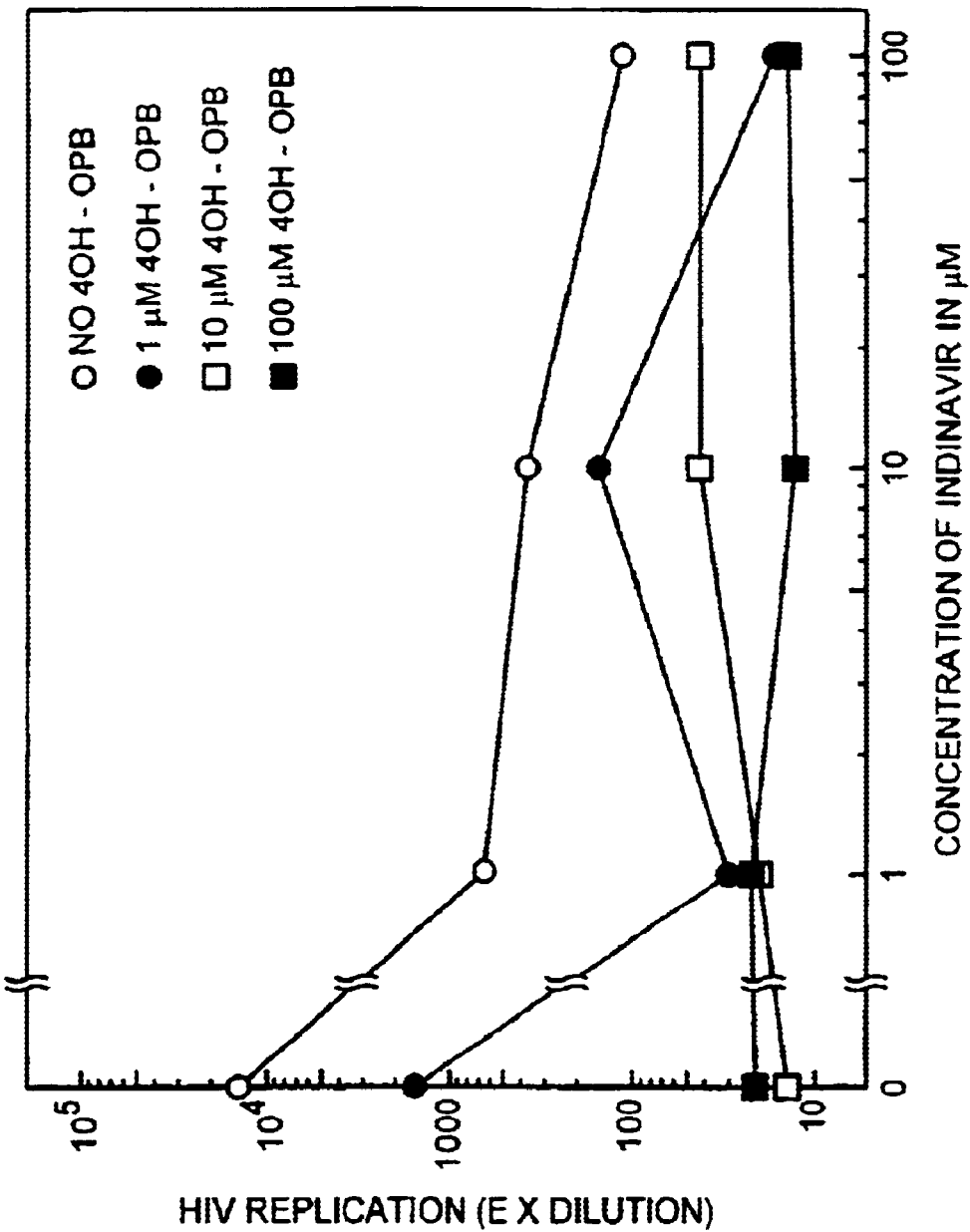

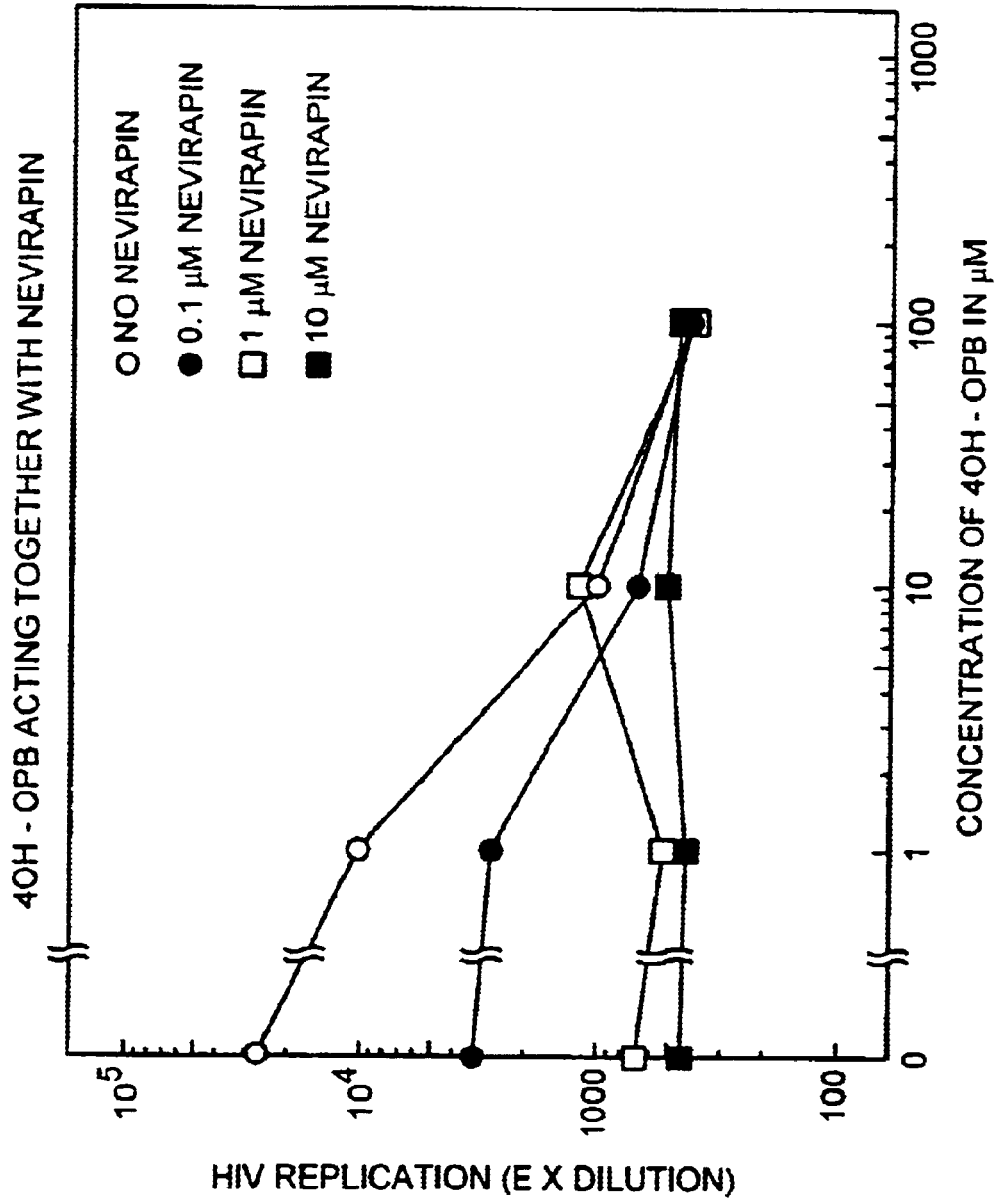

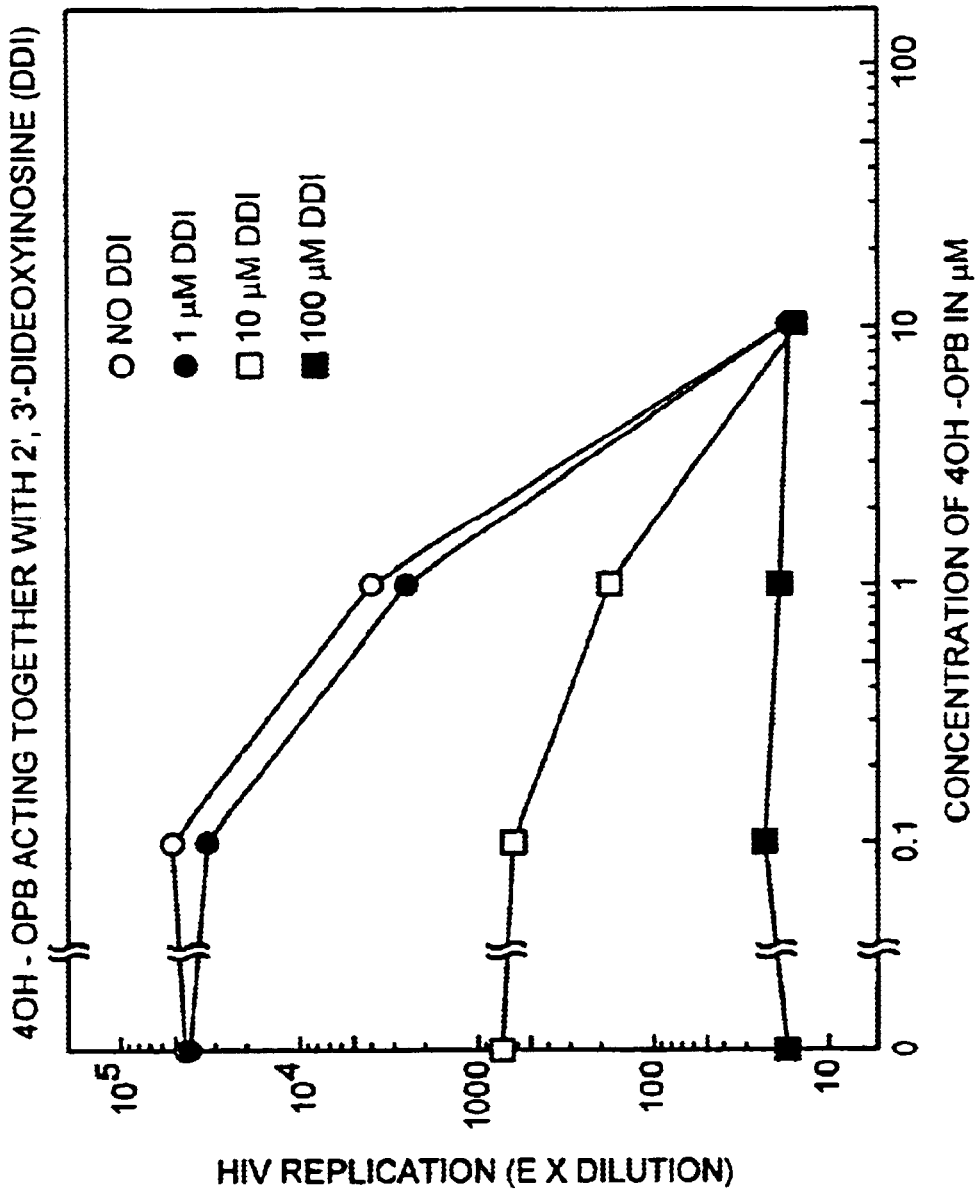

PYRAZOLIDINOL COMPOUNDS

The present invention relates to certain pyrazolidinols and their sulphur (i.e. thio/thiol) analogs and pharmaceutical compositions thereof for use in antiviral, e.g. anti-HIV therapy and as anti-inflammatories and immunomodulators.

Phenbutazone and oxyphenbutazone are 1,2-bis aromatic-3,5-pyrazolidinediones which have been used as non-steroidal anti-inflammatory drugs (NSAIDs)

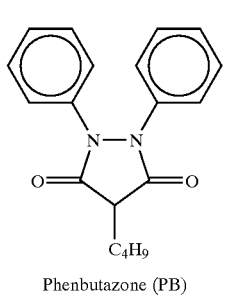
Phenbutazone (PB)

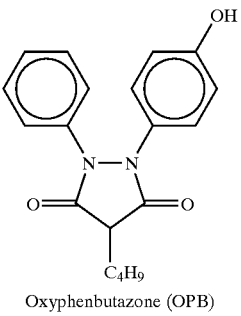
Oxyphenbutazone (OPB)

Other 3,5-pyrazolidinediones have likewise been proposed for use as NSAIDs (see for example U.S. Pat. No. 3,968,219 (Rahtz)) and the hydroxy-protected enol forms have been proposed as pro-drug forms of phenbutazone and oxyphenbutazone (see U.S. Pat. No. 4,117,232 (Bodor), U.S. Pat. No. 3,957,803 (Bodor), U.S. Pat. No. 4,169,147 (Bodor), U.S. Pat. No. 4,03,6845 (Bodor) and U.S. Pat. No. 4,139,709 (Bodor)).

In U.S. Pat. No. 4,956,377 (Miesch) it was proposed that this class of NSAIDs had utility as an antiviral agent, in particular for the treatment of HIV.

We have now surprisingly found that where the 4-carbon of the $N_2C_3$ ring carries an optionally protected hydroxy or thiol group, the compounds have very significantly enhanced antiviral, in particular anti-HIV, efficacy.

Thus viewed from one aspect the invention provides the use of an optionally hydroxy-protected 4-hydroxy or hydroperoxy-3,5-dioxo-pyrazolidine or an equivalent wherein a pyrazolidine ring attached oxygen is replaced by a sulphur, or a physiologically acceptable salt thereof, for the manufacture of a medicament for use in therapy or prophylaxis.

Where a particular 4-hydroxy or hydroperoxy-3,5-dioxo-pyrazolidine may exist in more than one stereoisomeric form, it may be used in single isomer form or as an isomer mixture, e.g. a racemic mixture.

Viewed from a further aspect, the invention provides an optionally hydroxy-protected 4-hydroxy or hydroperoxy-3, 5-dioxo-pyrazolidine or an equivalent wherein a pyrazolidine ring attached oxygen is replaced by a sulphur, or a physiologically acceptable salt thereof.

Viewed from a still further aspect the invention provides a method of treatment of the human or non-human (e.g. mammalian, reptilian or avian) body to combat an inflammatory or viral disease, preferably an immuno-deficiency viral disease in particular HIV, which method comprises administering to said body an optionally hydroxy-protected 4-hydroxy or hydroperoxy-3,5-dioxo-pyrazolidine or an equivalent wherein a pyrazolidine ring attached oxygen is replaced by a sulphur, or a physiologically acceptable salt thereof.

Viewed from a still further aspect, the invention provides a pharmaceutical composition comprising an optionally hydroxy-protected 4-hydroxy or hydroperoxy-3,5-dioxo-pyrazolidine or an equivalent wherein a pyrazolidine ring attached oxygen is replaced by a sulphur, or a physiologically acceptable salt thereof, together with at least one pharmaceutically acceptable carrier or excipient.

The applicants have found that oxyphenbutazone, as commercially available, contains minute quantities of certain impurities, presumably as a result of undesired oxidative breakdown. One of these, present at about 0.4% wt, is 4-butyl-4-hydroxy-2(p-hydroxyphenyl)-1-phenyl-3,5-pyrazolidinediones (hereinafter "4-OH-OPB"), i.e.

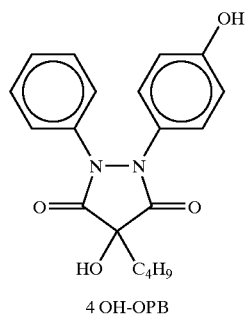
4 OH-OPB

4-OH-OPB is of course a compound according to the invention and thus it should be understood that references to the 4-hydroxy compounds of the invention, their use and compositions thereof should not be taken to include references to such compounds when in intimate admixture with overwhelmingly larger quantities of a 3,5-pyrazolidinedione which carries no optionally protected 4-hydroxy or 4-thiol group. By overwhelmingly larger is meant a relative weight ratio of at least 98:2. In general, the compounds of the invention should not desirably be used in intimate admixture with larger quantities (i.e. a relative weight ratio of more than 50:50) of such compounds carrying no O or S attached group at the 4-position, and more desirably they should not be used with such compounds present in greater than 10:90 weight ratio.

The compounds of the invention, hereinafter referred to as pyrazolidinols for convenience, will preferably be of formula I

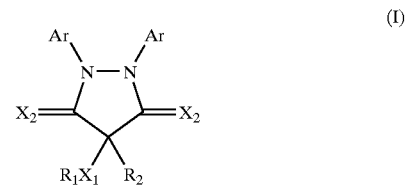

(where each $X_2$, which may be the same or different is O or S, preferably O;

$X_1$ is O, OO or S, preferably O or S, most preferably O;

$R_1$ is hydrogen or a hydroxyl or thiol protecting group (e.g. an acyl group, preferably containing up to 6 carbons, e.g. an acyl group such as an alkylcarbonyl group, for example acetyl), preferably hydrogen;

$R_2$ is hydrogen or more preferably a carbon attached organic group containing up to 10 carbons, e.g. an alkyl, alkenyl, alkynyl, alkaryl, aralkyl or aralkenyl group, optionally substituted, e.g. by a sulphonyl group; and each Ar, which may be the same or different, is a homo or heterocyclic aromatic group, optionally substituted, e.g. by $C_{1-6}$ alkyl or alkoxy groups) or a salt thereof.

In the compounds of the invention 0, 1 or 2 of the $X_1$ and $X_2$ groups may be S. It is thought that it is especially preferred that one thio $X_2$ group be present.

In the compounds of the invention, the $R_2$ group is preferably other than hydrogen and may for example be straight chain, branched, cyclic or cyclic-attached-to-straight chain. Preferably it is an alkyl or alkenyl group, especially a C1an alkyl or alkenyl group, e.g. n-propyl, n-butyl, n-pentyl or 1-methyl-but-2-en-4-yl or an aralkyl (e.g. benzyl) or alkaryl (e.g. methylphenyl) or arylsulphonylalkyl (eg phenylsulphonylethyl) group.

Where $R_1$ in the compounds of the invention is other than hydrogen it is preferably a metabolically labile hydroxy- or thiol-protecting group, which yields a physiologically tolerable $R_1OH$ metabolite. Acyl groups are preferred in this regard.

In the compounds of formula I, where each $X_2$ is oxygen and one Ar is phenyl, the other Ar is preferably other than phenyl e.g. parahydroxyphenyl.

A wide range of hydroxy- and thiol-protecting groups however is known from the literature (see McOmie, "Protective groups in organic chemistry", Plenum, 1973 and Greene, "Protective groups in organic synthesis", Wiley Interscience, NY, 1981) and many compounds of formula I in which $R_1$ is a protecting group may be useful as intermediates in the production of compounds of formula I in which $R_1$ is hydrogen.

The Ar groups in the compounds of formula I are preferably 5 to 7 membered aromatic rings, optionally carrying a fused aromatic ring and optionally substituted on ring atoms, for example by $C_{1-6}$ alkyl groups but especially by electron withdrawing substituente, e.g. hydroxy, thiol, phenyl, $C_{1-6}$ alkoxy, cyano, halo (e.g. Cl, F, Br or I), protected hydroxy, or protected thiol. Ring heteroatoms will generally be selected from O, N and S, preferably with a single ring heteroatom in any aromatic Ar heterocycle. Ar is preferably phenyl optionally substituted, especially in the para-position by —$X_2$—$R_1$ or Cl (where —$X_1$—$R_1$ is as defined above). Especially preferably one Ar is phenyl and the other is p-hydroxy-phenyl.

Where the substitution of the pyrazolidinols of the invention is such that they may form addition salts with acids or bases, the addition salts which have physiologically tolerable counter ions are of course preferred, e.g. sodium, organic amine, halides, phosphates, hydrogen carbonates, etc.

The pyrazolidinols of the invention may particularly advantageously be used in combination therapy with other antiviral, especially anti-HIV, agents, in particular reverse transcriptase inhibitors and/or protease inhibitors, e.g. zidovudine, didanovine, zalcitabine, stavudine, lamivudine, nevirapine, delavirdine, indinavir, ritonavir, nelfinavir, hydroxyurea kolchicine, AZT and 2',3'-dideoxyinosine (ddI). Such combination therapy forms a further aspect of the present invention.

A drawback of traditional combination therapy, has often been that even under intensive antiviral treatment with a combination of drugs, a little HIV production continues and is unaffected by treatment. The compounds of the invention may prove to have an effect in reducing this residual HIV production when given in combination with other antiviral agents. This may be due to the increasing antiviral effect which has been seen in long term cell culture experiments and which may counteract any development of resistance to the compounds.

The pyrazolidinols of the invention may be prepared by oxidation of a corresponding compound where $R_1X_1$ is replaced by hydrogen; by reaction of a corresponding compound where $R_1X_1$ is $HX_1$ with a hydroxy or thiol protecting agent to introduce a non-hydrogen $R_1$ group, or by condensation of a hydrazine derivative with an optionally protected 2-hydroxy-propane dioic acid ester (or a sulphur analog), e.g. by condensation of a compound of formula II

(II)

with a compound of formula III

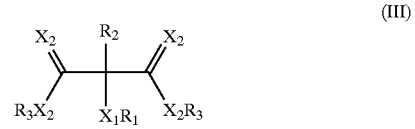
(III)

where $R_1$, $R_2$, $X_1$, $X_2$ and Ar are as hereinbefore defined and $X_2R_3$ is a leaving group, for example where $R_3$ is an alkyl group, e.g. $C_{1-6}$ alkyl group.

Alternatively, a compound of formula II may be condensed with a compound of formula IV

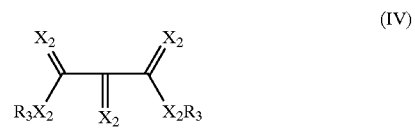
(IV)

(where $X_2$ and $R_3$ are as defined above) and then reacted with an alkylating agent, e.g. $(R_2)_2Zn$ to produce a compound of formula I in which $X_1R_1$ is OH or SH.

For administration, the pyrazolidinols of the invention may be formulated in any convenient form, e.g. tablets, coated tablets (e.g. delayed release tablets), capsules, solutions, suspensions, dispersions, syrups, powders, sprays, suppositories, transdermal patches, gels, emulsions and creams. Administration may be via any convenient route, e.g. oral, rectal, transdermal, nasal, subcutaneous, intravenous, intramuscular, etc. Oral administration, e.g. of tablets or capsules is preferred. The pyrazolidinols may be formulated together with conventional pharmaceutical carriers, diluents or excipients, e.g. aqueous carriers (for example water for injections), binders, fillers, stabilizers, osmolality adjusting agents, effervescing agents, pH modifiers, viscosity modifiers, sweeteners, lubricants, emulsifiers, flavours, coating agents (e.g. gastric juice resistant coatings), etc. Where any formulation results in a loss of compound, this loss should be calculated and the dosage increased proportionally to obtain the desired active concentration.

The dosage of the pyrazolidinols given according to the invention will depend on the size and species of the subject being treated but will generally be in the range of 0.05 to 2000 mg/day, more particularly 0.5 to 1000 mg/day, especially 1 to 100 mg/day, preferably with administration being effected once, twice, three times or four times daily. For mice, doses of up to 2000 mg/kg (corresponding to 20 mM maximal concentration in extracellular fluid) could be given before lethal dosage was reached, ie effective treatment doses were up to 200000 times smaller than the lethal dose.

For regular, e.g. continuous daily treatment according to the invention, the daily dosage of the pyrazolidinol will preferably be in the range 5 nmol to 2 μmol/kg bodyweight, more preferably 100 nmol to 1.5 μmol/kg, especially 500 nmol to 1 μmol/kg.

Inhibition of virus production may be achieved by small intermittent doses of pyrazolidinol, and are expected to induce inhibition of the virus after a latency of about 11 weeks. Subsequently, inhibition may be expected to level out, should resistance to the compound develop. Such doses may be administered at a frequency of 1–14 days, preferably 7 days. The doses should be equivalent to a concentration in plasma/tissue fluid of from 100–1000 nM and may be obtained by ingestion or injection of from 0.7–7 mg in a 70 Kg human.

However, in a particularly preferred embodiment of the invention, a pyrazolidinol according to the invention is administered at a dose sufficient to suppress T-lymphocyte (CD4 and CD8 cell) growth (e.g. a daily dose of 0.1 to 10 µmol/kg) for a period of 1 to 14 days, preferably 2 to 7 days at intervals of at least 3 months, preferably at least 9 months, e.g. 10 to 18 months. In this way the patient's immune system may be "refreshed" by removal of the preponderance of T-lymphocytes directed to HIV antigens. Such a treatment indeed is novel and forms a further aspect of the invention. Viewed from this aspect the invention provides a method of combatting HIV infection which comprises administering to an HIV-infected patient a T-lymphocyte growth suppressing agent, e.g. a pyrazolidinol, in an amount sufficient to suppress T-lymphocyte growth in said patient for a period sufficient to reduce the T-lymphocyte concentration in the lymphatic system, e.g. the lymph nodes, in said patient by at least 25%, more preferably at least 50%, said administration being repeated at intervals of at least 3 months, preferably at least 9 months.

High tissue concentrations intended to give an immunomodulating effect should preferably be given for limited periods at doses of 1 µM or above in plasma/tissue fluid. Such doses and lengths of administration will vary according to the condition of each patient and may be decided with the guidance of tests such as the count of HIV memory subsets of T8 and T4. As stated above, the goal of treatment according to this aspect of the invention should be to reduce subsets which are found to be too prevalent without overly affecting naive T-cells.

In order to obtain the desired reduction of HIV specific lymphocytes (e.g. HIV memory CD8 and CD4 lymphocytes) without overly affecting naive T-lymphocytes or other essential blood cells, monoclonal antibodies against the unwanted subtypes may also be administered. Further, drugs such as kolchicine and/or hydroxy-urea may be included in the intermittent intensive treatment. Such additional drugs are anticipated to have a somewhat different immunomodulating effect to the compounds of the invention and so may be used advantageously in combination with pyrazolidinols for refreshing the immune system.

Besides HIV, the pyrazolidinols of the invention may be used to combat other viral infections, especially retroviral infections but also infections by togaviridea, reoviridea, picornaviridea, hantaviridea, orthomyxoviridea, paramyxoviridea, mononegaviralis, viral hepatitis, haemorrhagic fevers, flaviviridea, viral encephalitis, coronaviridea, calciviridea, adenoviridea, papovaviridea, arboviridea, pox virus, rhabdoviridea, herpes virus and arenaviridea. The pyrazolidinols of the invention may in particular be used to combat viral infections of CD4 cells, e.g. HIV-1, HIV-2, RTLV-I, UTLV-II and herpes viruses, for example to combat AIDS, T-cell tumours (e.g. Sezary Syndrome, mycosis fungoides and T-cell lymphoma, and particularly CD4 cell tumours), tropic spastic paraparesis, and Karposi's sarcoma. Moreover despite not being of the accepted formula for NSAIDs (which would require an acid proton in place of $R_1X_1$ at the 4-position), they may be used as anti-inflammatory drugs. All these uses form aspects of the invention.

Due to the immunomodulating effect of the compounds of the invention, they are expected to have uses in control of other immune-system related diseases, such as auto immune diseases and as immunosuppressants. In particular, the compounds of the invention are expected to have a positive effect on the generation of autoimmune diseases, on developed autoimmune diseases and on diseases related to such diseases, such as Addison's disease, Bechet's syndrome, diaetes mellitus and other endocrine diseases, haemolytic anaemia, lupus erythematosus, multiple sclerosis, myasthenia gravis, pernicious anaemia, polyglandular deficiency, polymyositis, dermatomyositis, testicular failure, thrombocytopenic purpura, Crohns disease, ulcerative colitis, rheumatic disorders (e.g. rheumatoid arthritis) etc.

The effect of the compounds of the invention on the immune system may also be that of imunosuppression. Such an effect may be used, for example, to control rejection of a medical transplant or implant. In particular, the compounds may be used to reduce rejection following tissue or organ transplant.

Various 4-hydroxy-3,5-dioxo-pyrazolidines are known in the literature (although not for medical purposes such as HIV therapy). These are compounds of formula V

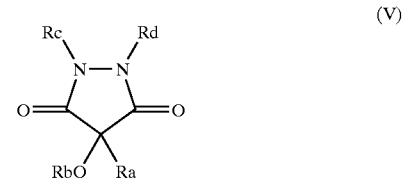

(V)

where $R_a$ to $R_d$ are as set out in Table 1 below:

TABLE 1

| $R_a$ | $R_b$ | $R_c$ | $R_d$ |
|---|---|---|---|
| H | H | H | $C_6H_5$ |
| H | H | $C_6H_5$ | $C_6H_5$ |
| $CH_3$ | H | H | $C_6H_5$ |
| $CH_3$ | H | H | —$CH_2$—$C_6H_5$ |
| $CH_3$ | H | H | p-$CH_3O$—$C_6H_4$ |
| $CH_3$ | H | H | p-Cl—$C_6H_4$ |
| $C_2H_5$ | H | H | $C_6H_5$ |
| $C_2H_5$ | H | $C_6H_5$ | $C_6H_5$ |
| $C_2H_5$ | H | H | N-methyl-piperidin-4-yl |
| $iC_2H_2$ | H | H | $C_6H_5$ |
| $nC_3H_7$ | H | H | $C_6H_5$ |
| $nC_3H_2$ | H | $C_6H_5$ | $C_6H_5$ |
| $nC_3H_7$ | H | H | 5-phenyl-triazol-1-yl |
| $C_4H_9$ | H | H | $C_6H_5$ |
| $C_4H_9$ | H | $C_6H_5$ | $C_6H_5$ |
| $C_4H_9$ | H | $C_6H_5$ | p-OH—$C_6H_4$ |
| $C_4H_9$ | OH | $C_6H_5$ | $C_6H_5$ |
| $C_4H_9$ | OH | $C_6H_5$ | p-OH—$C_6H_4$ |
| $C_4H_9$ | H | H | N-methyl-piperidin-4-yl |
| $C_5H_{11}$ | H | H | $C_6H_5$ |
| $C_5H_{11}$ | H | $C_6H_5$ | $C_6H_5$ |
| $C_5H_{11}$ | H | H | 5-phenyl-triazol-1-yl |
| Cyclohexyl | H | H | $C_6H_5$ |
| Phenyl | H | H | $C_6H_5$ |
| Phenyl | H | $C_6H_5$ | $C_6H_5$ |
| Benzyl | H | H | $C_6H_5$ |
| Benzyl | H | $C_6H_5$ | $C_6H_5$ |
| $CH_3CO(CH_2)_2$ | H | $C_6H_5$ | $C_6H_5$ |
| $(CH_3)_2C=CH—$ | H | $C_6H_5$ | $C_6H_5$ |
| $(CH_2)_2C=CHCH_2$ | H | $C_6H_5$ | $C_6H_5$ |
| $C_6H_5SCH_2CH_2$ | H | $C_6H_5$ | $C_6H_5$ |
| Pyrrolidin-1-yl | H | $C_6H_5$ | $C_6H_5$ |
| Piperidin-1-yl | H | $C_6H_5$ | $C_6H_5$ |
| Morpholin-4-yl | H | $C_6H_5$ | $C_6H_5$ |

Such compounds are thus not claimed per se herein; however their use and pharmaceutical compositions containing them do form part of the scope of the invention.

The invention will now be illustrated further by the following non-limiting Examples and by reference to the Figures, in which:

FIG. 3 shows the effect of 4-butyl-4-hydroxy-2(p-hydroxyphenyl)-1-phenyl-3,5-pyrazolidinedione (4OH-OPB) when used in combination with indinavir; and;

FIG. 4 shows the effect of 4-butyl-4-hydroxy-2(p-hydroxyphenyl)-1-phenyl-3,5-pyrazolidinedione (4OH-OPB) when used in combination with nevirapine;

Figure 2:
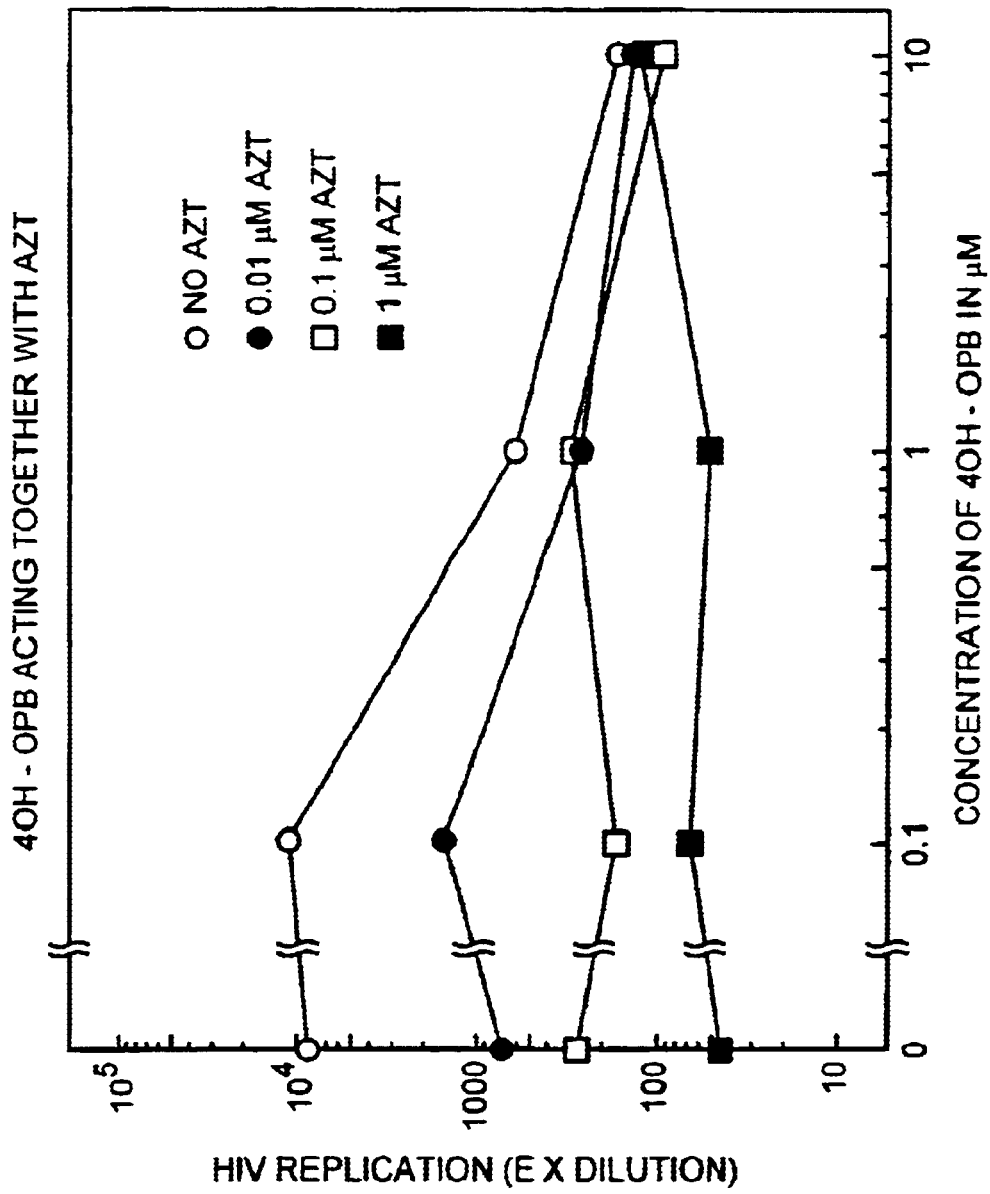
FIG. 2 shows the effect of 4-butyl-4-hydroxy-2(p-hydroxyphenyl)-1-phenyl-3,5-pyrazolidinedione (4OH-OPB) when used in combination with AZT.

A similar effect to those shown in FIGS. 2–4 is seen when OPB is used in combination with 2',3'-dideoxyinosine (daI).

FIG. 5 shows a 4OH-OPB acting together with 2',3'-dideoxyinosine (DDL).

EXAMPLE 1

Preparation of 4-Methoxyazobenzene

A mixture of 4-phenylazophenol (9.9 g; 50 mmol), iodomethane (7.1 g; 50 mmol), potassium carbonate (6.9 g; 50 mmol), and acetone (100 ml) was refluxed 48 h. After evaporating off the solvent, the residue was dissolved in water (25 ml), diethyl ether (50 ml) and THF (30 ml). The aqueous layer was extracted with ether (3×20 ml) and the combined organic solutions were washed with saturated NaCl solution (1×20 ml) and dried ($MgSO_4$). After filtration and evaporation, the residue was recrystallized from 96% ethanol to give 8.7 g (82%).

EXAMPLE 2

Preparation of 1-(4-Methoxyphenyl)-2-phenylhydrazine

Zinc powder (10.0 g; 0.15 mol) was added to a stirred mixture of 4-methoxyazobenzene (4.24 g; 20.0 mmol) in 96% ethanol (75 ml) and saturated $NH_4Cl$ solution (2.0 ml) at 0° C. (bath temperature). Two more portions of saturated $NH_4Cl$ solution (2.0 ml) were added at 1.5 h intervals. The yellowish solution was poured into cold water (100 ml) and filtered. The residue was extracted with methylene chloride (5×50 ml). The combined aqueous phases were extracted with methylene chloride (3×25 ml). The combined organic solutions were,dried ($Na_2SO_4$), filtered and evaporated to give 4.3 g crude 1-(4-methoxyphenyl)-2-phenylhydrazine as a reddish oil.

EXAMPLE 3

Preparation of 4-(1-Butyl)-1-(4-methoxyphenyl)-2-phenyl-3,5-pyrazolidinedione

Diethyl butylmalonate (4.33 g; 20.0 mmol) was added to a stirred solution of sodium (0.46 g; 20.0 mmol) in absolute ethanol (20 ml), followed by crude 1-(4-methoxyphenyl)-2-phenylhydrazine (4.3 g; 20 mmol max.) in absolute ethanol (5 ml). About ⅔ of the ethanol was distilled off and xylene (20 ml) was added to the residue. The reaction mixture was heated to 140–145° C. (bath temperature) for 15 h to distill off the rest of the ethanol. The reaction mixture was cooled to 0° C. (bath temperature) and poured into ice water (ca. 100 ml). The aqueous layer was extracted with $CH_2Cl_2$ (2×15 ml); the extracts were discarded. The cold aqueous layer was acidified with 6 H HCl (5 ml) and extracted with $CH_2Cl_2$ (3×10 ml). The combined extracts were washed with water (2×10 ml) and dried ($MgSO_4$). Filtration and evaporation gave 3.84 g amber oil. Purified by flash chromatography on a 130×65 mm silica gel 60 column eluted with ethyl acetate-heptane (1:3) to give 1.45 g (21%) colourless oil.

$^1$H NMR (200 MHz; $CDCl_3$): δ 0.90 (3H, t, J=7.5 Hz), 1.25–1.6 (4H, m), 2.0–2.15 (2H, m), 3.37 (3H, t, J=6.0 Hz), 3.69 (3H, s), 6.81 (2H, d, J=8.4 Hz), 7.22 (2H, d, J=8.6 Hz), 7.1–7.35 (5H, m). $^{13}$C NMR (50 MHz; $CDCl_3$): δ 13.6, 22.2, 27.5, 27.6, 45.6, 54.7, 112.9, 121.6, 123.3, 125.4, 127.1, 127.4, 133.9, 156.5, 168.2, 168.7.

EXAMPLE 4

Preparation of 1,2-Diphenyl-4-(4-methoxyphenyl)-3,5-pyrazolidinedione

Prepared from 1,2-diphenylhydrazine (3.70 g; 20.0 mmol), diethyl 2-(p-tolyl)malonate (5.0 g; 20.0 mmol), and sodium (0.46 g; 20.0 mmol) using the procedure of Example 3. The crude product crystallized on standing and was recrystallized twice from absolute ethanol to give 1.22 g (18%), mp 184–185° C.

$^1$H NMR (200 MHz; $CDCl_3$). δ 2.31 (3H, s), 4.51 (1H, s), 7.1–7.4 (14H, m). $^{13}$C NMR (50 MHz; $CDCl_3$): δ 21.1, 51.9, 122.7, 126.9, 128.3, 129.0, 129.9, 135.8, 138.3, 168.6.

EXAMPLE 5

Preparation of 4-Benzyl-1,2-diphenyl-3,5-pyrazolidinedione

Prepared from 1,2-diphenylhydrazine 14.60 g; 25.0 mmol), diethyl benzylmalonate (5.0 g; 20 mmol), and sodium (0.46 g; 20.0 mmol) using the procedure of Example 3. The crude product was recrystallized from absolute ethanol to gave 3.51 g (50%), mp 136–137° C. [lit. 137–138° C. (Beil. III/IV, 24, 1463)].

$^1$H NMR (200 MHz; $CDCl_3$): δ 3.41 (2H, d, J=4.6 Hz), 3.63 (1H, t, J=5.0 Hz), 6.85–7.3 (10H, m). $^{13}$C NMR (50 MHz; $CDCl_3$): δ 33.9, 48.5, 123.2, 126.9, 127.3, 128.6, 128.7, 129.9, 135.2, 135.4, 169.3.

EXAMPLE 6

Preparation of 4-Allyl-1,2-diphenyl-3,5-pyrazolidinedione

Prepared from 1,2-diphenylhydrazine (5.2 g; 28.0 mmol), diethyl allylmalonate (5.0 g; 25.0 mmol), and sodium (0.58 g; 25.0 mmol) using the procedure of Example 3. The crude product was recrystallized from absolute ethanol to give 2.21 g (30%) tan crystals, mp 135–137° C.

$^1$H NMR (200 MHz; $CDCl_3$): δ 2.82 (2H, t, J=6.0 Hz), 3.46 (2H, t, J=5.4 Hz), 5.1–5.3 (2H, dd), 5.7–5.95 (1H, m), 7.1–7.3 (10H, m). $^{13}$C NMR (50 MHz; $CDCl_3$): δ 31.7, 46.4, 119.9, 122.7, 126.8, 128.9, 131.7, 135.6, 169.5.

EXAMPLE 7

Preparation of 4-(1-Butyl)-4-hydroxy-1-(4-hydroxyphenyl)-2-phenyl-3,5-pyrazolidinedione (4OH-OPB)

Method A

Oxyphenbutazone.$H_2O$ (1 mmol), 30% $H_2O_2$ (0.7 mL), 1N NaOH (0.1 mL) and methanol 13.5 mL) are allowed to stand for 13 hours at ambient temperature. The mixture is then poured into 5% HCl (20 mL) and extracted with ethyl acetate (2×20 mL). The ethyl acetate phase is separated, dried over sodium carbonate and the solvent is removed under reduced pressure without heating The residue is subjected to flash chromatography (silica/ethyl acetate). The title product is recrystallized from ethyl acetate.

Method B

A solution of oxyphenbutazone hydrate (2.0 g; 5.8 mmol), 35% hydrogen peroxide solution (3.4 ml; 40 mmol), and 1 M sodium hydroxide solution (0.6 ml; 0.6 mmol) in methanol (20 ml) was allowed to stand for 24 h at ambient temperature. The mixture was acidified with 1 M HCl solution (50 ml) and extracted with ethyl acetate (4×15 ml). The combined extracts were washed with saturated NaCl solution (1×10 ml) and dried ($MgSO_4$). After filtration and evaporation, the residue was purified by flash chromatography on a 100×65 mm silica gel 60 column eluted with ethyl acetate-heptane (1:1), taking 50-ml fractions, giving 1.3 g (66%).

$^1$H NMR (200 MHz; $CDCl_3$): δ 0.88 (3H, t, J 6.6 Hz), 1.25–1.5 (4H, m), 1.95–2.05 (2H, m), 6.49 (1H, br s), 6.75 (2H, d, J=8.9 Hz), 7.12 (2H, d, J=8.9 Hz), 7.1–7.35 (5H, m). $^{13}$C NMR (50 MHz; $CDCl_3$): δ 13.6, 22.3, 24.3, 36.2, 72.8, 114.3, 121.9, 123.8, 125.3, 125.7, 127.2, 133.5, 154.6, 169.0, 169.5.

EXAMPLE 8

Preparation of 4-(1-Butyl)-4-hydroxy-1-(4-methoxyphenyl)-2-phenyl-3,5-pyrazolidinedione Prepared from 4-(1-butyl)-1-(4-methoxyphenyl)-2-phenyl-3,5-pyrazolidinedione (1.35 g; 3.8 mmol), 35% $H_2O_2$ (4.3 ml; 50 mmol), 2 M NaOH (0.35 ml; 0.7 mmol), and methanol (50 ml) using the procedure of Example 7. Purified by flash chromatography on a 110×65 mm silica gel 60 column eluted with ethyl acetate-heptane (1:1) to give 0.7 g (52%).

$^1$H NMR (200 MHz; $CDCl_3$): δ 0.65 (3H, t, J=6.2 Hz), 1.2–1.5 (4H, m), 2.0–2.1 (2H, m), 3.69 (3H, s), 4.8 (1H, br s), 6.77 t2H, d, J=9.0 Hz), 7.19 (2H, d, J=9.0 Hz), 7.1–7.35 (5H, m). $^{13}$C NMR (50 MHz; $CDCl_3$): δ 13.5, 22.3, 24.3, 36.7, 54.7, 73.3, 113.0, 122.1, 123.8, 125.8, 126.1, 127.5, 133.0, 156.7, 168.5, 169.0.

EXAMPLE 9

Preparation of 1,2-Diphenyl-4-hydroxy-4-[2-(phenylsulfonyl)ethyl]-3,5-pyrazolidinedione Prepared from (±)-sulfinpyrazone (2.02 g; 5.0 mmol), 35% $H_2O_2$ (4.3 ml; 50 mmol), 2 M NaOH (0.35 ml; 0.7 mmol), and methanol (50 ml) using the procedure of Example 7. Purified by flash chromatography on a 130×65 mm silica gel 60 column eluted with ethyl acetate-acetic acid 120:1) to give 60 mg (4%).

$^1$H NMR (200 MHz; $CDCl_3$): δ 2.1–2.5 (2H, m), 3.0–3.7 (2H, m), 5.5 (1H, br s), 6.4–7.9 (15H, m). $^{13}$C NMR (50 MHz; $CDCl_3$): δ 28.7, 47.5, 70.2, 121.5. 122.9, 125.8, 126.5, 127.4, 127.7, 127.9, 129.9, 133.3, 133.4, 136.9, 139.2, 167.5, 168.0.

EXAMPLE 10

1,2-Diphenyl-4-hydroxy-4-(4-methylphenyl)-3,5-pyrazolidinedione

A mixture of 1,2-diphenyl-4-(4-methylphenyl)-3,5-pyrazolidinedione (1.10 g; 3.2 =mol), 35% $H_2O_2$ (0.47 ml; 5.5 mmol), and acetic acid (40 ml) was stirred 16 days at room temperature. Sodium metabisulfite (1.0 g) was added and excess acetic acid evaporated off. The residue was dissolved in hot ethyl acetate (25 ml) and benzene (25 ml) and filtered. After cooling to room temperature, the mixture was filtered and the residue recrystallized from 50% aqueous ethanol (20 ml) to give 0.58 g (53%).

$^1$H NMR (200 MHz; $CDCl_3$): δ 2.32 (3H, s), 7.0–7.45 (14H, m). $^{13}$C NMR (50 MHz; $CDCl_3$): δ 21.1, 57.9, 123.9, 124.5, 127.0, 128.3, 128.4, 128.7, 130.4, 135.6, 139.0, 168.5.

EXAMPLE 11

Preparation of 4-Benzyl-1,2-diphenyl-4-hydroxy-3,5-pyrazolidinedione

Prepared from 4-benzyl-1,2-diphenyl-3,5-pyrazolidinedione (3.3 g; 9.6 mmol), 35% $H_2O_2$ (1.4 ml; 16.3 mmol), and acetic acid (50 ml) using the procedure of Example 10 to give 1.0 g (30%).

$^1$H NMR (200 MHz; $CDCl_3$): δ 3.30 (2H, s), 6.75–7.3 (15M, m). $^{13}$C NMR (50 MHz; $CDCl_3$): δ 43.1, 75.4, 123.0, 126.7, 127.5, 128.4,, 130.2, 132.1, 134.7, 170.1.

EXAMPLE 12

Antiviral Activity of 4OH-OPB (Example 7)

Figure 1:
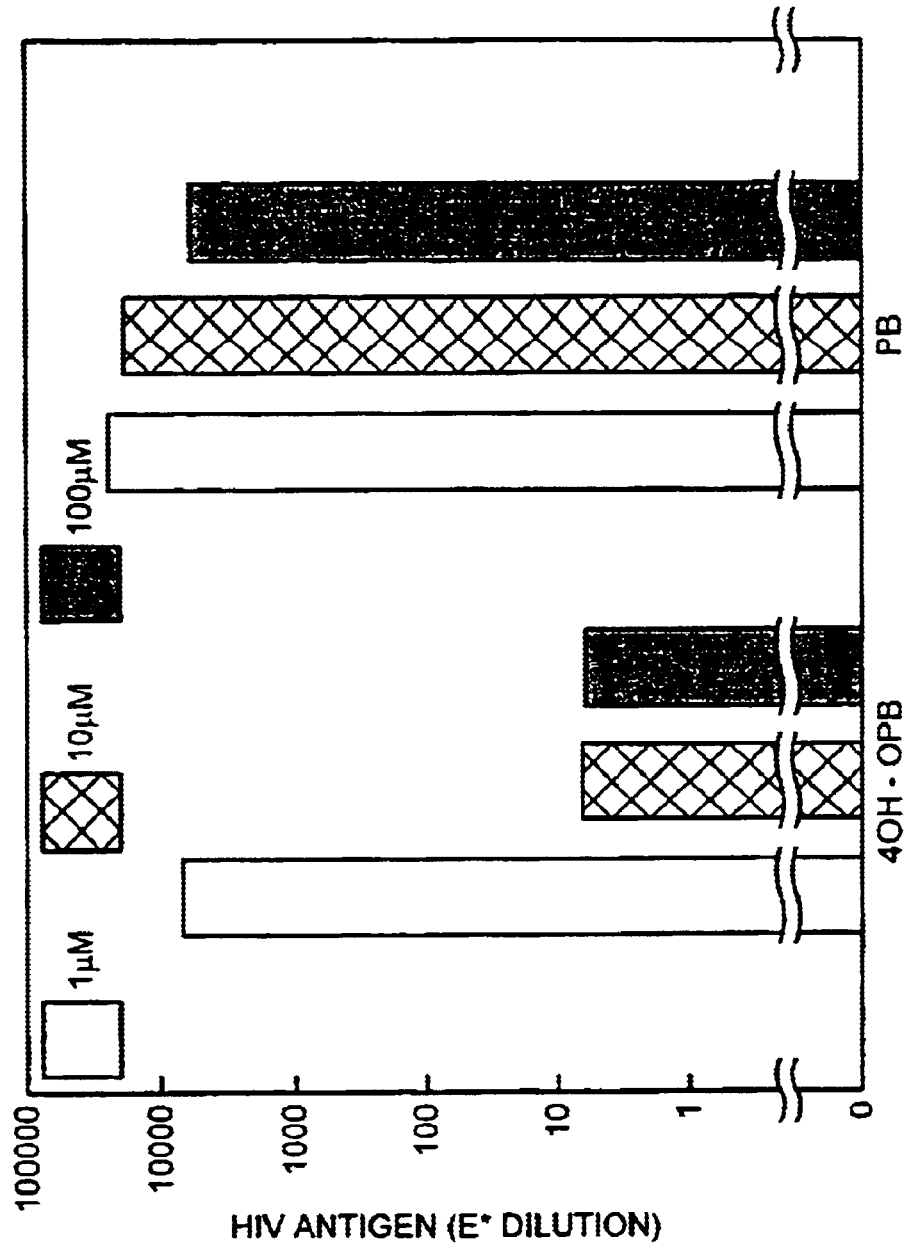
FIG. 1 shows the HIV antigen concentration in human. CD4 cells infected,with HIV and treated with 4-butyl-4-hydroxy-2(p-hydroxyphenyl)-1-phenyl-3,5-pyrazolidinedione (4OH-OPB) or phenbutazone (PB) at various concentrations.

4OH-OPB was added to cultures of growing MT4 cello (a human CD4 cell line). HIV-1, stored in the culture medium at −75° C. was thawed and added in an amount which infected about 1 in 7 cells in each culture. The virus was absorbed to the cells for 2.3 hours at ambient temperature where after the cultures were centrifuged at 1200 rpm, the medium was removed, the cells were suspended in fresh-growth medium and 4OH-OPB was added to concentrations of 1, 10 and 100 μM (diluted in medium from a stock solution of 20 mM in DMSO). After 72 hours the HIV antigen concentration was determined using Abbott's test. By way of comparison phenbutazone (PB) was tested analogously. The results are shown in FIG. 1 and demonstrate inhibition of virus production by 4OH-OPB at concentrations above the lowest tested.

EXAMPLE 13

Combination Activity Effect with 4OH-OPB

Cell culture experiments were carried out as in Example 12, but in place of 4OH-OPB (0–100 μM) was added:
  i) 4OH-OPB (0–10 μM) with AZT (0–1 μM)
  ii) 4OH-OPB (0–100 μM) with Indinavir (0–100 μM)
  iii) 4OH-OPB (0–100 μM) with Nevirapin (0–10 μM)
  iv) 4OH-OPB (0–10 μM) with ddI (0–100 μM)

The results are shown in FIGS. 2–5 respectively and demonstrate the enhanced anti-HIV effect of 4OH-OPB in combination with other anti-viral agents.

EXAMPLE 14

| Preparation of capsules for oral use | |
|---|---|
| 4-OH OPB (Example 7) | 50 mg |
| Amylum maydis | q.s. |

The powder is mixed and filled into hard gelatin capsules (Capaugel size 00).

EXAMPLE 15

| Preparation of tablets | |
|---|---|
| | Gram |
| 4-OH OPB (Example 7) | 200 |
| Lactose | 85 |
| Polyvinylpyrrolidone | 5 |
| Starch | 42 |
| Talcum powder | 15 |
| Magnesium stearate | 3 |

4-OH OPB and lactose are screened through a 0.15 mm sieve and mixed together with an aqueous solution of polyvinyl-pyrrolidone. The mass is granulated and the dried (40° C.) granulate is mixed with starch, talcum powder and magnesium atearate. The granulate is compressed into tablets. The tablet diameter is 11 mm, the tablet weight is 350 mg and each tablet contains 200 mg 4-OH OPB.

EXAMPLE 16

Preparation of a Suspension for Rectal Administration

Methyl 2-hydroxybeznzoate (70 mg3 and propyl-p-hydroxybenzoate (15 mg) are dissolved in water (100 ml) at 90° C. After cooling to 30° C., methyl cellulose (2 g) is added and the mixture is agitated for 3 hours. 1 gram 4-OH OPB (Example 7) is screened through a 0.15 mm sieve, and dispersed in the solution under vigorous stirring. The suspension is filled in a 100 ml tube. The suspension contains 10 mg 4-OH OPB/ml.

EXAMPLE 17

| Preparation of oral suspension | |
|---|---|
| | Gram |
| 4OH OPB (Example 7) | 10 |
| Carboxymethyl cellulose | 1.5 |
| Sorbitol | 200 |
| Sodium benzoate | 1.0 |
| Orange essence | 0.3 |
| Apricot essence | 0.7 |
| Ethanol | 50 |
| Water | 236.5 |

Carboxymethyl cellulose, sorbitol and sodium benzoate are dissolved in water with stirring for 2 hours. A solution of the essences in ethanol is added. 4-OH OPB is screened through a 0.15 mm sieve and dispersed in the solution under vigorous stirring. The suspension (10 gram) is filled in a 20 ml tube. Each tube contains 200 mg 4-OH OPS.

EXAMPLE 16

Mouse Toxicity 20 g mice were given single doses of 4OH-OPB (20 mM in DMSO) intraperitoneally. Doses of 1 to 100 $\mu$M (in ECF), corresponding to 0.29 to 29 $\mu$M/kg bodyweight, produced no toxic effect. Furthermore, injection of 4OH-OPB could be increased to 2000 mg/kg (corresponding to 20 mM in the extracellular fluid) before the mice started to die (6 out of 10 died at 2000 mg/kg). Thus the concentrations that effectively inhibit HIV replication in cell cultures are up to 200000 times lower than the lethal dose in mice.

What is claimed is:

1. A method of treatment of the human or non-human body to combat an inflammatory disease, autoimmune disease or tissue rejection, wherein said method comprises administering to said body a compound of formula I.

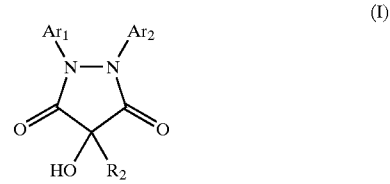

(I)

wherein $Ar_1$ and $Ar_2$ are phenyl optionally substituted with hydroxy, thiol, $C_1$–$C_6$ alkoxy, cyano or halo and $R_2$ is H or $C_1$–$C_{10}$ alkyl, provided that the relative weight ratio of any 3,5-pyrazoladine dione not having a 4-hydroxy group (impurity) to said compound of formula I is not more than 50 parts impunity to 50 parts formula I.

2. A method as claimed in claim 1 wherein said disease is selected from Addison's disease, Bechet's syndrome, diabetes mellitus, haemolytic anasmia, lupus erythematosus, multiple sclerosis, myasthenia gravis, pernicious anaemia, polyglandular deficiency, polymyositis, dermatomyositis, testicular failure, thrombocytopenic purpura, Crohns disease, ulcerative colitis and rheumatoid arthritis.

3. A method as claimed in claim 2 wherein said disease is diabetes mellitus or rheumatoid arthritis.

4. A method as claimed in claim 1 wherein $Ar_1$ is phenyl, $Ar_2$ is p-hydroxy phenyl, and $R_2$ is $C_4H_9$.

5. A method as claimed in claim 1 wherein said relative weight ratio of any 3,5-pyrazoladine dione not having a 4-hydroxy group to said compound of formula I is not more than 10 parts impurity to 90 parts formula I.

* * * * *